United States Patent
Carinci et al.

(12) 
(10) Patent No.: US 10,605,879 B2
(45) Date of Patent: Mar. 31, 2020

(54) MAGNETIC RESONANCE METHOD AND APPARATUS FOR ARTIFACT PREVENTION IN FAST 3D SPIN ECHO SEQUENCES

(71) Applicant: Siemens Healthcare GmbH, Erlangen (DE)

(72) Inventors: Flavio Carinci, Erlangen (DE); Dominik Paul, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/251,424

(22) Filed: Jan. 18, 2019

(65) Prior Publication Data

US 2019/0227139 A1 Jul. 25, 2019

(30) Foreign Application Priority Data

Jan. 22, 2018 (DE) .......................... 10 2018 200 900

(51) Int. Cl.
*G01R 33/561* (2006.01)
*G01R 33/54* (2006.01)
*A61B 5/055* (2006.01)

(52) U.S. Cl.
CPC .......... *G01R 33/5618* (2013.01); *A61B 5/055* (2013.01); *G01R 33/543* (2013.01)

(58) Field of Classification Search
CPC .... G01R 33/5618; G01R 33/543; A61B 5/055
See application file for complete search history.

(56) References Cited

U.S. PATENT DOCUMENTS

| 2009/0212773 A1* | 8/2009 | Feinberg | G01R 33/4818 |
| | | | 324/309 |
| 2013/0099784 A1* | 4/2013 | Setsompop | G01R 33/54 |
| | | | 324/309 |

* cited by examiner

*Primary Examiner* — Gregory H Curran
(74) *Attorney, Agent, or Firm* — Schiff Hardin LLP

(57) ABSTRACT

In a method and magnetic resonance (MR) apparatus for creating an MR 3D image dataset, spin echo sequences are used to acquire two raw datasets that are each undersampled, wherein the excitation pulses or the refocusing pulses radiated in the data acquisitions have an opposite phase for the two raw datasets. These two raw datasets are combined into a combined 3D raw dataset that is not undersampled, and a weighting matrix is calculated for use in calculating the raw data points that were not acquired in the first raw dataset and the raw data points not acquired in the second raw dataset. A first complete raw dataset and second complete raw dataset are thereby calculated, which are then combined. The MR 3D data is then reconstructed from tis combined raw dataset.

19 Claims, 5 Drawing Sheets

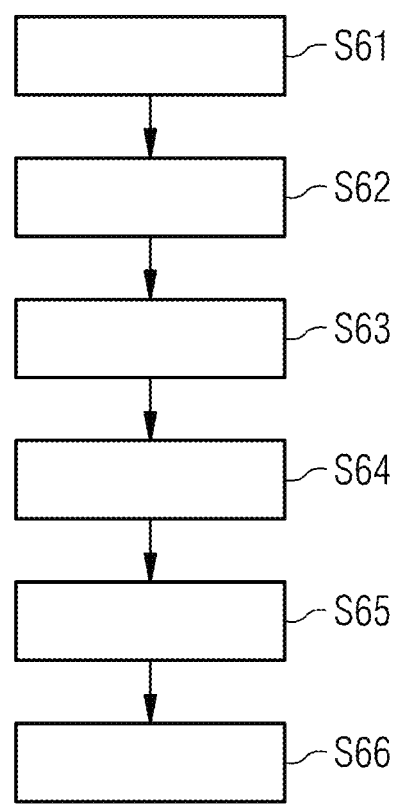

MAGNETIC RESONANCE METHOD AND APPARATUS FOR ARTIFACT PREVENTION IN FAST 3D SPIN ECHO SEQUENCES

BACKGROUND OF THE INVENTION

Field of the Invention

The present invention concerns a method for creating a 3D magnetic resonance (MR) image dataset of a subject under examination, and an associated MR system, and a non-transitory, electronically readable data storage medium.

Description of the Prior Art

In MR imaging, a fast 3D spin echo sequence is known in which, after a radio-frequency (RF) excitation pulse, a refocusing pulse train of up to several hundred refocusing pulses is radiated, some of these refocusing pulses having reduced refocusing flip angles. This imaging sequence was originally designed with non-selective RF excitation pulses, which means that raw MR data can be acquired therewith only from entire volumes can be acquired thereby. In order to be able to use such 3D multi-spin echo sequences in regions under examination such as the spine, hip or pelvis, a selective operating mode for this sequence was introduced, in which a selective RF excitation pulse is used with a train of non-selective refocusing pulses.

Using the non-selective refocusing pulses after the excitation pulse, however, results in FID (free induction decay) signals within the echo train from regions outside the selectively excited volume. This can cause artifacts that interfere with the imaging and make the diagnosis harder.

SUMMARY OF THE INVENTION

An object of the present invention is to improve such fast 3D spin-echo based imaging sequences so that these artifacts resulting from the FID signal are reduced.

According to a first aspect of the invention, this object is achieved by a method for acquiring a 3D MR image dataset for a subject under examination using a number of reception coils. The method includes radiating at least one first RF excitation pulse into the subject under examination followed by one or more first non-frequency-selective RF refocusing pulses in order to generate at least one first spin echo. The one or more first spin echoes are acquired in a first raw dataset in the three-dimensional raw dataspace (k-space) using multiple reception coils, in which process the first raw dataset of the raw dataspace is filled only partially with raw data such that the first raw dataset is not filled (sampled) completely with raw data according to the Nyquist theorem. In addition, at least one second RF excitation pulse is radiated into the subject under examination, followed by one or more second non-selective RF refocusing pulses in order to generate the one or more second spin echoes. In this case, the second RF refocusing pulses each have an opposite phase to the first RF refocusing pulses. Alternatively, it is possible for the first and second RF excitation pulses to have an opposite phase. The one or more second spin echoes are acquired in a second raw dataset in the three-dimensional raw dataspace using the multiple reception coils, in which process, for the second raw dataset, said dataset is filled only partially with raw data such that the second portion is not completely sampled with raw data according to the Nyquist theorem. The first raw dataset and second raw dataset in total fill the raw dataspace with raw data fully according to the Nyquist theorem. The first raw dataset and the second raw dataset are brought together into a combined three-dimensional raw dataset that is filled with raw data fully according to the Nyquist theorem. Then a weighting matrix for parallel imaging is calculated on the basis of the combined 3D raw dataset for use in calculating (estimating) the raw data points that were not acquired in the first raw dataset and the raw data points not acquired in the second raw dataset. The raw data points that were not acquired in the first raw dataset are created (synthesized by estimation) using the weighting matrix and the raw data acquired in the first raw dataset. These calculations for the two raw datasets can be performed both in the raw dataspace and in the image space, for instance in this case using the SENSE technique.

It is thus possible to calculate a first complete raw dataset from the raw data points created for the first raw dataset and from the raw data acquired in the first raw dataset. In addition, the raw data points not acquired in the second raw dataset are created (synthesized by estimation) using the weighting matrix and the raw data points acquired in the second raw dataset, so a second complete raw dataset is calculated from the raw data points created for the second raw dataset and from the raw data points acquired in the second raw dataset. The first complete raw dataset and the second complete raw dataset are added together to form a combined complete raw dataset, to which a known transformation (reconstruction) algorithm is applied so as to create the 3D MR image dataset.

Acquiring the two raw datasets having the opposite phase so that together they fill the entire raw dataspace means that the acquisition time is shortened, because there is no need to fill the entire raw dataspace twice fully with raw data. Also, it is possible to use the combined 3D raw dataset to calculate the weighting matrix which is then needed for calculating the first complete raw dataset and the second complete raw dataset. It is then possible to combine these two complete raw datasets to create the 3D MR image dataset, in which then the artifacts resulting from the FID signals are reduced or entirely suppressed. Using the refocusing pulses in the second raw dataset with opposite phase, i.e. with a phase rotated through 180°, means that the FID signals outside the excited subject under examination add destructively and cancel out, with the result that now just the spin echoes provide the major signal component. In addition, the measurement time is reduced because both the first raw dataset and the second raw dataset are undersampled.

The first complete raw dataset and the second complete raw dataset can be added by complex addition in the raw dataspace or in the image space (domain).

It is possible to acquire the first and second raw datasets such that they have no shared raw data points. Half of the 3D raw dataset is preferably acquired in the first raw dataset, with the other half acquired in the second raw dataset, resulting overall in the 3D raw dataspace being acquired in full, but only once.

The first complete raw dataset and the second complete raw dataset can be produced using reconstruction techniques (that include the aforementioned estimation of the "missing" data points) from parallel imaging, for instance the GRAPPA technique or using the CAIPIRINHA technique. The missing data points in the two raw datasets are estimated by these techniques and using the weighting matrix that was calculated on the basis of the combined 3D raw dataset.

The first RF excitation pulse and the second RF excitation pulse are preferably frequency-selective excitation pulses, although the method can also be used with non-frequency-selective RF excitation pulses.

The first raw dataset and the second raw dataset can be acquired separately from one another in succession or in what is known as the interleaved pattern, in which portions of the second raw dataset are acquired before the acquisition of the first raw dataset has completely finished.

The first raw dataset and the second raw dataset preferably each occupy half of the entire raw dataspace, and respectively fill each half.

The associated MR system has an MR data acquisition scanner with a number of reception coils, an RF controller, and at least one image sequence controller, which also controls the multiple reception coils and the RF controller such that the acquisition of the raw dataspace is performed as above. The MR system also has a processor that calculates the 3D MR image dataset as described above.

The present invention also encompasses a non-transitory, computer-readable data storage medium that, when the storage medium is loaded into a computer or computer system of a magnetic resonance imaging apparatus, cause the computer or computer system to operate the magnetic resonance imaging apparatus in order to implement any or all embodiments of the method according to the invention, as described above.

The features described above and the features described below can be used not only in the corresponding explicitly presented combinations, but also in other combinations unless explicitly stated otherwise.

BRIEF DESCRIPTION OF THE DRAWINGS

FIG. 6 is a flowchart for creating the 3D MR image dataset having reduced FID artifacts according to the invention.

DESCRIPTION OF THE PREFERRED EMBODIMENTS

The present invention is described in detail below using preferred embodiments with reference to the accompanying drawings. The same reference numbers denote identical or similar elements in the figures. In addition, the figures are schematic representations of various embodiments, and the elements depicted in the figures are not necessarily shown to scale. The elements shown in the figures are depicted in a way that makes their function and purpose clear to those skilled in the art. The connections shown in the figures between functional units or other elements can also be implemented as an indirect connection. Each connection can be wireless or hardwired. Functional units can be implemented as hardware, software or as a combination of hardware and software.

Figure 1:
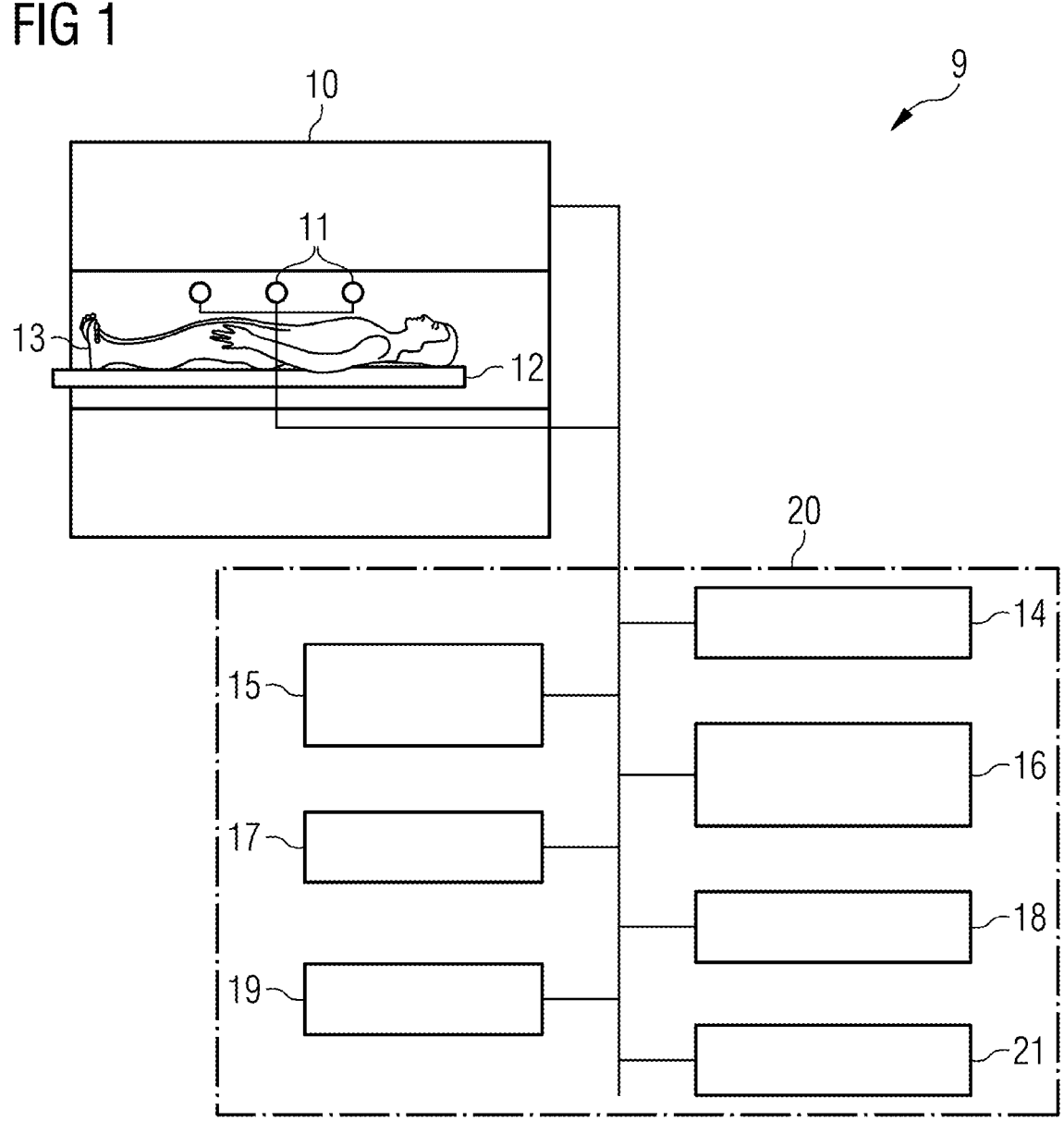
FIG. 1 is a schematic illustration representation of an MR system that is operable according to the invention to execute 3D spin-echo sequences in a short acquisition time and without FID artifacts.

An MR system 9 is explained with reference to FIG. 1. The MR system 9 is operable so as to produce 3D spin-echo based MR images having reduced FID artifacts, as will be explained below. The MR system 9 has an MR data acquisition scanner with a basic field magnet that generates a polarization field B0, into which a person under examination on a table 12 is moved in order to acquire spatially encoded magnetic resonance signals from the person 13, using a number of reception coils 11. The invention uses a technique known as parallel imaging, in which the MR signals are acquired simultaneously by the multiple reception coils 11. By applying radio frequency pulses and by switching magnetic field gradients in the scanner 10, certain nuclear spins in the patient are given a magnetization that causes those excited nuclear spins to be deflected from the direction dictated by the polarization field B0. As those excited nuclear spins relax, they emit RF signals, called magnetic resonance signals that are detected by the reception coils 11. Complex numbers, representing the detected MR signals, are entered into a memory organized as k-space, as raw data, which are then transformed into image data, as described below.

The principles of how MR images are produced by applying RF pulses and switching magnetic field gradients in various combinations and sequences are known to those skilled in the art, and thus need not be explained in more detail herein.

The MR system has a control computer 20 that controls the MR system 9. The control computer 20 includes an RF controller 14 that controls and generates the RF pulses for deflecting the magnetization. A gradient controller 15 is provided that controls and switching of the necessary magnetic field gradients. An image sequence controller 16 controls the sequence of the magnetic field gradients, the signal detection, and the RF pulses, and hence indirectly operates the gradient controller 15, the reception coils 11 and the RF controller 14. An operator can control the MR system 9 via an input interface 17, and MR images and other information needed for control can be displayed on a display monitor 18. A processor 19 is provided for controlling the various components of the control computer 20. In addition, a memory 21 is provided in which program modules and/or program code can be stored that can control the process flow of the MR system 9 when executed by the processor 19. As explained below, the image sequence controller 16 and the processor 19 are designed such that a 3D raw dataspace is filled in a specific manner with spin echoes in order to produce a 3D MR image dataset, which prevents the occurrence of FID artifacts, in a shorter acquisition time than the prior art.

Figure 2:
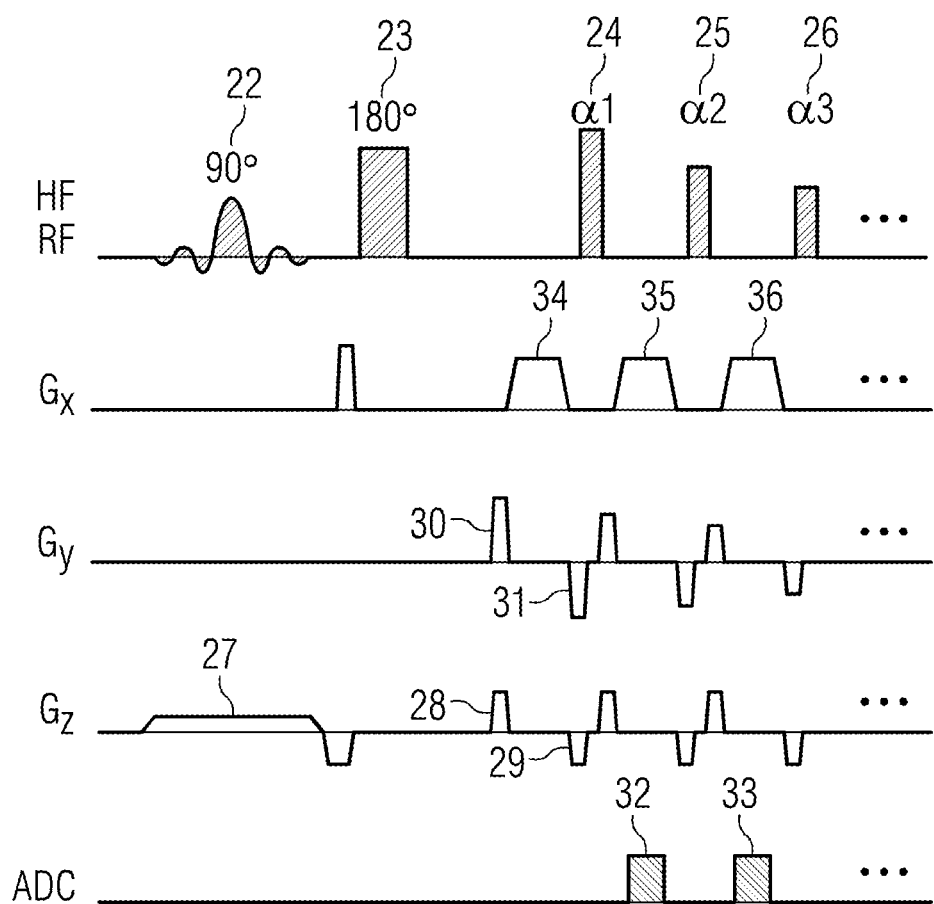
FIG. 2 is a sequence diagram of the imaging sequence used in the acquisition of the raw data according to the invention.

FIG. 2 schematically shows the 3D MR imaging sequence. After a frequency-selective RF excitation pulse 22, a first RF refocusing pulse 23 is radiated, followed by further non-selective RF refocusing pulses 24-26, which can have a smaller focusing angle than 180°, in order to reduce the energy radiated into the person under examination. In the slice-selection direction $G_z$, the slice-selection gradient 27 for exciting the desired region in the subject under examination is switched simultaneously with the excitation pulse 22. The gradient switchings 28 and 29 needed for the phase encoding are additionally performed, likewise the gradient switchings 30 and 31 in the phase-encoding direction. In the readout direction, the readout gradients 34-36 are switched during the signal readouts 32, 33, wherein the first echo cannot be read out.

Figure 3:
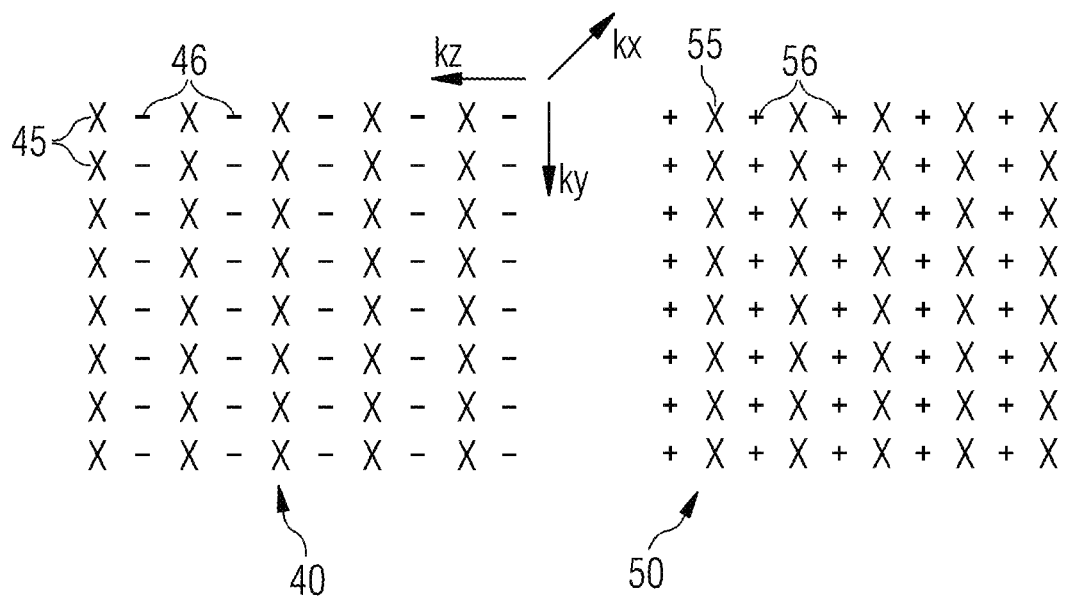
FIG. 3 schematically illustrates the acquisition pattern used to create the first raw dataset and the second raw dataset according to the invention.

It is now explained, with additional reference to FIG. 3, how an imaging sequence of this type is used to acquire the raw dataspace. In a first step, as shown on the left of FIG. 3, only the first half of the raw dataspace is acquired, where reference sign 45 is used to represent the raw data lines that are not acquired, which run into the drawing plane in the $k_x$ direction, as it is a 3D dataset. The figure also shows the raw data 46 that are acquired by a first phase cycle, which means that the refocusing pulses 23-26 have a first phase relative to the excitation pulse. If the RF excitation pulse is applied in the x direction, for example, all the refocusing pulses can be radiated in the y direction. This is thus a sampling pattern that is similar to the IPAT pattern, but without acquisition of reference lines. This produces a first raw dataset 40.

In addition, in a second step, a second raw dataset 50 is acquired, which is shown on the right in FIG. 3, where in turn 55 is used to represent the raw data lines that are not acquired, while 56 represents the data acquired in the second raw dataset 50, in which process the phase of the refocusing pulses differs by 180° from the phase of the refocusing pulses for the acquisition of the raw data points 46. Referring to FIG. 2, this means that the refocusing pulses are acquired once using a first phase, and a second time for the second raw dataset 50 using a second, opposite phase, i.e. a phase offset of 180°. For example, if the refocusing pulses 23-26 are radiated along the +y direction for the first raw dataset, then it is possible when applying the radiation for the second raw dataset, to radiate said pulses along the −y direction. Alternatively, it is possible to have an opposite phase for the excitation pulses.

The two raw datasets 40, 50 are then acquired such that ultimately the 3D raw dataspace is acquired in full, although once only, since each of the two raw datasets of FIG. 3 is undersampled.

Figure 4:
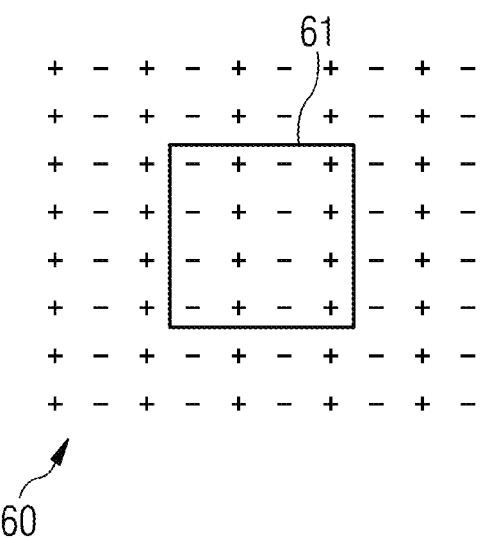
FIG. 4 schematically illustrates how the combined 3D raw dataset, which is used to calculate the weighting matrix, is created from the combination of the two raw datasets of FIG. 3 according to the invention.

As FIG. 4 shows, it is then possible to combine the two raw datasets 40 and 50 to produce a combined 3D raw dataset as represented in FIG. 4 by reference numeral 60. In this process, the acquired raw data from the two raw datasets 40 and 50 are combined. When using an opposite phase for the excitation pulses, the two raw datasets are then subtracted in the combination. From the combined 3D raw dataset 60, it is then possible to calculate from a central region 61 of the combined raw dataset a weighting matrix, for example what is known as the GRAPPA kernel, which can then be used to calculate the missing regions in the two raw datasets 40 and 50, namely the raw data points having reference signs 45 and 55. Hence a first complete raw dataset also is calculated using the weighting matrix, or kernel, and a second complete raw dataset is calculated using the weighting matrix. These two complete raw datasets can then be added in a complex addition in order to prevent the FID artifacts. It is also possible for the two raw dataspaces to be added by complex addition, and then reconstructed.

Since a number of echo trains are normally necessary in order to acquire the raw dataspace in full, the two raw datasets need not be acquired successively in time but can also be acquired with a technique known as an interleaved pattern.

Option A (conventional pattern):
$R_{1,+}, R_{2,+}, \ldots R_{n/2,+}, R_{n/2+1,-}, R_{n/2+2,-}, \ldots R_{n,-}$
Option B (interleaved pattern):
$R_{1,+}, R_{2,-}, R_{3,+}, R_{4,-} \ldots R_{n-1,+}, R_{n,-}$ where R denotes the number of echo trains, and + and − each ref er to the phase of the refocusing pulse, where N is the number of repetitions.

Figure 5:
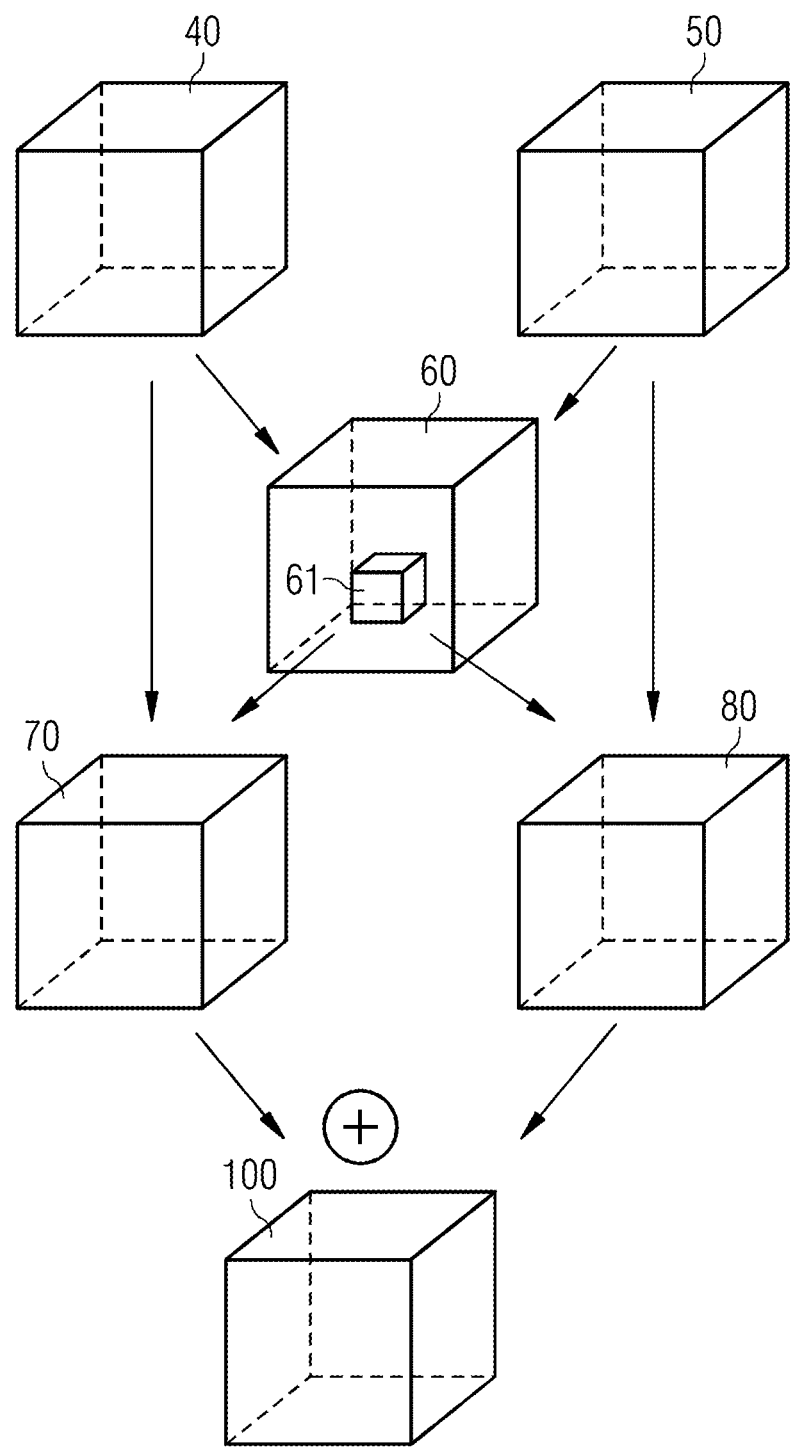
FIG. 5 schematically illustrates the different datasets acquired in creating the 3D MR dataset having reduced FID artifacts, and which further datasets are calculated according to the invention.

FIG. 5 shows schematically once again the datasets acquired or calculated in the various steps. The first raw dataset 40 is acquired using the first RF excitation pulses and the first non-frequency-selective refocusing pulses, with the second raw dataset 50 being acquired using the second spin echoes and the opposite refocusing pulses. These can then be combined into a combined 3D raw dataset 60, wherein the weighting matrix can be calculated using the central region 61. This weighting matrix can then be used to calculate a first complete raw dataset 70 using the acquired raw data in the raw dataset 40, and likewise the second complete raw dataset 80 can be calculated using the raw data points measured in the second raw dataset and the weighting matrix. By combining these two complete raw datasets it is possible to produce the 3D raw dataset 100, in which process the addition is a complex addition.

In the pattern employed in FIG. 4, raw data points or raw data lines were alternately acquired and not acquired in the kz or ky direction. The method can be applied arbitrarily in the kz or ky direction, however, i.e. the two raw dataspaces 40 and 50 can be formed in any way provided they are not filled entirely with raw data and the two raw datasets 40 and 50 do not overlap at the raw data points.

For calculating the first complete raw dataset and the second complete raw dataset, other parallel imaging techniques such as CAIPIRINHA can be used other than the GRAPPA technique.

FIG. 6 re-summarizes the steps. In a step S61, the first raw dataset 40 is acquired by applying the first RF excitation pulses and the first non-frequency-selective RF refocusing pulses. This first raw dataset is not filled fully with raw data and is thus undersampled according to the Nyquist theorem. In step S62, the second raw dataset 50 is likewise acquired, as was explained in association with FIGS. 2 and 3. As explained above, the steps S61 and S62 need not be performed in succession but can also be performed in parallel in what is known as the interleaved method, in which portions of the first raw dataset 40 and portions of the second raw dataset 50 are acquired alternately. Then in the step S63, the acquired raw data is combined into the combined 3D raw dataset 60. In the step S64, the weighting matrix, or the kernel, can then be calculated on the basis of the combined 3D raw dataset. It is thereby ultimately possible, in step S65, to calculate the first complete raw dataset 70 and the second complete raw dataset 80 respectively, wherein the 3D MR image dataset 100 can finally be calculated, in the step S66, by adding these complete raw datasets. The MR images produced using this 3D MR image dataset exhibit no FID artifacts or only highly suppressed FID artifacts, with it being possible to reduce the measurement time overall at least by a factor of 2 compared with the prior art.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for producing a magnetic resonance (MR) 3D image dataset of an examination subject, comprising:
    operating a radio-frequency (RF) radiator of an MR data acquisition scanner to radiate a first RF excitation pulse into the examination subject;
    also operating said RF radiator of said MR data acquisition scanner to radiate a first non-frequency-selective RF refocusing pulse, that causes a first spin echo to be produced from the examination subject;

with a plurality of RF reception coils of said MR data acquisition scanner, acquiring said first spin echo as a first raw dataset entered into an electronic memory organized as a 3D raw dataspace, by filling only a portion of said 3D raw dataspace with raw data from said first spin echo, so that said first raw dataset is undersampled according to the Nyquist theorem;

operating the RF radiator to radiate a second RF excitation pulse into the subject;

after radiating said second RF excitation pulse, operating the RF radiator to radiate a second non-frequency-selective RF refocusing pulse that causes a second spin echo to be produced from the examination subject, said first and second RF refocusing pulses having opposite phases compared to each other;

with said plurality of RF reception coils, acquiring said second spin echo as a second raw dataset entered in said 3D raw dataspace in said electronic memory, by filling only another portion of said 3D raw dataspace with raw data from said second spin echo, so that said second raw dataset is undersampled according to the Nyquist theorem, with said first raw dataset and said second raw dataset in total filling an entirety of said 3D raw dataspace so that said entirety of the 3D raw dataspace is completely sampled according to the Nyquist theorem;

in a processor, combining said first raw dataset and said second raw dataset to form a combined 3D raw dataset, which is completely filled with raw data according to the Nyquist theorem;

in said processor, using the combined 3D raw dataset to calculate a weighting matrix;

in said processor, using said weighting matrix and the raw data acquired in the first raw dataset to estimate raw data points that were not entered into said 3D raw dataspace when acquiring said first raw dataset;

in said processor, calculating a first complete raw dataset from the raw data points estimated for the first raw dataset and the raw data acquired in the first raw dataset;

in said processor, using said weighting matrix and the raw data acquired in the second raw dataset to estimate raw data points that were not entered into said 3D raw dataspace when acquiring said second raw dataset;

in said processor, calculating a second complete raw dataset from the raw data points estimated for the second raw dataset and the raw data acquired in the second raw dataset;

in said processor, adding said first complete raw dataset and said second complete raw dataset to produce a summed complete raw dataset; and in said processor, applying a reconstruction algorithm to said summed complete raw dataset to produce said MR 3D image dataset.

2. A method as claimed in claim 1 comprising, in said processor, adding said first complete raw dataset and said second complete raw dataset by complex addition in the raw dataspace.

3. A method as claimed in claim 1 comprising, in said processor, adding said first complete raw dataset and said second complete raw dataset by complex addition in the image domain, using phase information in said first and second complete raw datasets.

4. A method as claimed in claim 1 comprising operating said MR data acquisition scanner to acquire said first and second raw datasets so that said first and second raw datasets have no shared raw data points.

5. A method as claimed in claim 1 comprising calculating said first complete raw dataset and said second complete raw dataset using a parallel imaging reconstruction technique.

6. A method as claimed in claim 1 comprising operating said RF radiator of said MR data acquisition scanner to radiate each of said first and second RF excitation pulses as a frequency-selective excitation pulse.

7. A method as claimed in claim 1 comprising operating said MR data acquisition scanner to acquire all of said first raw dataset before acquiring all of said second raw dataset.

8. A method as claimed in claim 1 comprising operating said MR data acquisition scanner to acquire at least a portion of said second raw dataset before finishing complete acquisition of said first raw dataset.

9. A method as claimed in claim 1 comprising operating said MR data acquisition scanner to acquire said first and second raw datasets so that said first and second raw datasets have a same size.

10. A magnetic resonance (MR) apparatus comprising:

an MR data acquisition scanner comprising a radio-frequency (RF) radiator and a plurality of RF reception coils;

a computer configured to operate said RF radiator of an MR data acquisition scanner to radiate a first RF excitation pulse into the examination subject;

said computer being configured to also operate said RF radiator of said MR data acquisition scanner to radiate a first non-frequency-selective RF refocusing pulse, that causes a first spin echo to be produced from the examination subject;

said computer being configured to operate said MR data acquisition scanner to acquire said first spin echo with said plurality of RF reception coils, as a first raw dataset entered into an electronic memory organized as a 3D raw dataspace, by filling only a portion of said 3D raw dataspace with raw data from said first spin echo, so that said first raw dataset is undersampled according to the Nyquist theorem;

said computer being configured to operate the RF radiator to radiate a second RF excitation pulse into the subject;

after radiating said second RF excitation pulse, said computer being configured to operate the RF radiator to radiate a second non-frequency-selective RF refocusing pulse that causes a second spin echo to be produced from the examination subject, said first and second RF refocusing pulses having opposite phases compared to each other;

said computer being configured to operate said MR data acquisition scanner to acquire said second spin echo with said plurality of RF reception coils, as a second raw dataset entered in said 3D raw dataspace in said electronic memory, by filling only another portion of said 3D raw dataspace with raw data from said second spin echo, so that said second raw dataset is undersampled according to the Nyquist theorem, with said first raw dataset and said second raw dataset in total filling an entirety of said 3D raw dataspace so that said entirety of the 3D raw dataspace is completely sampled according to the Nyquist theorem;

said computer being configured to combine said first raw dataset and said second raw dataset to form a combined 3D raw dataset, which is completely filled with raw data according to the Nyquist theorem;

said computer being configured to use the combined 3D raw dataset to calculate a weighting matrix;

said computer being configured to use said weighting matrix and the raw data acquired in the first raw dataset to estimate raw data points that were not entered into said 3D raw dataspace when acquiring said first raw dataset;

said computer being configured to calculate a first complete raw dataset from the raw data points estimated for the first raw dataset and the raw data acquired in the first raw dataset;

said computer being configured to use said weighting matrix and the raw data acquired in the second raw dataset to estimate raw data points that were not entered into said 3D raw dataspace when acquiring said second raw dataset;

said computer being configured to calculate a second complete raw dataset from the raw data points estimated for the second raw dataset and the raw data acquired in the second raw dataset;

said computer being configured to add said first complete raw dataset and said second complete raw dataset to produce a summed complete raw dataset; and said computer being configured to apply a reconstruction algorithm to said summed complete raw dataset to produce said MR 3D image dataset.

11. An MR apparatus as claimed in claim 10 wherein said computer is configured to add said first complete raw dataset and said second complete raw dataset by complex addition in the raw dataspace.

12. An MR apparatus as claimed in claim 10 wherein said computer is configured to add said first complete raw dataset and said second complete raw dataset by complex addition in the image domain, using phase information in said first and second complete raw datasets.

13. An MR apparatus as claimed in claim 10 wherein said computer is configured to operate said MR data acquisition scanner to acquire said first and second raw datasets so that said first and second raw datasets have no shared raw data points.

14. An MR apparatus as claimed in claim 10 wherein said computer is configured to calculate said first complete raw dataset and said second complete raw dataset using a parallel imaging reconstruction technique.

15. An MR apparatus as claimed in claim 10 wherein said computer is configured to operate said RF radiator of said MR data acquisition scanner to radiate each of said first and second RF excitation pulses as a frequency-selective excitation pulse.

16. An MR apparatus as claimed in claim 10 wherein said computer is configured to operate said MR data acquisition scanner to acquire all of said first raw dataset before acquiring all of said second raw dataset.

17. An MR apparatus as claimed in claim 10 wherein said computer is configured to operate said MR data acquisition scanner to acquire at least a portion of said second raw dataset before finishing complete acquisition of said first raw dataset.

18. An MR apparatus as claimed in claim 10 wherein said computer is configured to operate said MR data acquisition scanner to acquire said first and second raw datasets so that said first and second raw datasets have a same size.

19. A non-transitory, computer-readable data storage medium encoded with programming instructions, said storage medium being loaded into a computer of a magnetic resonance (MR) apparatus comprising an MR data acquisition scanner, said programming instructions causing said computer system to:

operate a radio-frequency (RF) radiator of an MR data acquisition scanner to radiate a first RF excitation pulse into the examination subject;

also operate said RF radiator of said MR data acquisition scanner to radiate a first non-frequency-selective RF refocusing pulse, that causes a first spin echo to be produced from the examination subject;

with a plurality of RF reception coils of said MR data acquisition scanner, acquire said first spin echo as a first raw dataset entered into an electronic memory organized as a 3D raw dataspace, by filling only a portion of said 3D raw dataspace with raw data from said first spin echo, so that said first raw dataset is undersampled according to the Nyquist theorem;

operate the RF radiator to radiate a second RF excitation pulse into the subject;

after radiating said second RF excitation pulse, operate the RF radiator to radiate a second non-frequency-selective RF refocusing pulse that causes a second spin echo to be produced from the examination subject, said first and second RF refocusing pulses having opposite phases compared to each other;

with said plurality of RF reception coils, acquire said second spin echo as a second raw dataset entered in said 3D raw dataspace in said electronic memory, by filling only another portion of said 3D raw dataspace with raw data from said second spin echo, so that said second raw dataset is undersampled according to the Nyquist theorem, with said first raw dataset and said second raw dataset in total filling an entirety of said 3D raw dataspace so that said entirety of the 3D raw dataspace is completely sampled according to the Nyquist theorem;

combine said first raw dataset and said second raw dataset to form a combined 3D raw dataset, which is completely filled with raw data according to the Nyquist theorem;

use the combined 3D raw dataset to calculate a weighting matrix;

use said weighting matrix and the raw data acquired in the first raw dataset to estimate raw data points that were not entered into said 3D raw dataspace when acquiring said first raw dataset;

calculate a first complete raw dataset from the raw data points estimated for the first raw dataset and the raw data acquired in the first raw dataset;

use said weighting matrix and the raw data acquired in the second raw dataset to estimate raw data points that were not entered into said 3D raw dataspace when acquiring said second raw dataset;

calculate a second complete raw dataset from the raw data points estimated for the second raw dataset and the raw data acquired in the second raw dataset;

add said first complete raw dataset and said second complete raw dataset to produce a summed complete raw dataset; and apply a reconstruction algorithm to said summed complete raw dataset to produce said MR 3D image dataset.

* * * * *